(12) United States Patent
Li et al.

(10) Patent No.: US 10,937,971 B2
(45) Date of Patent: Mar. 2, 2021

(54) ORGANIC MONOMOLECULAR WHITE LIGHT MATERIAL, MANUFACTURING METHOD FOR THE SAME, AND OLED ELEMENT

(71) Applicants: Shenzhen China Star Optoelectronics Technology Co., Ltd., Shenzhen (CN); Sun Yat-Sen University, Guangzhou (CN)

(72) Inventors: Xianjie Li, Shenzhen (CN); Yuanchun Wu, Shenzhen (CN); Poyen Lu, Shenzhen (CN); Bingjia Xu, Guangzhou (CN); Haozhong Wu, Guangzhou (CN); Junru Chen, Guangzhou (CN); Leyu Wang, Guangzhou (CN); Zhenguo Chi, Guangzhou (CN); Yi Zhang, Guangzhou (CN); Jiarui Xu, Guangzhou (CN)

(73) Assignees: SHENZHEN CHINA STAR OPTOELECTRONICS TECHNOLOGY CO., LTD., Guangdong (CN); SUN YAT-SEN UNIVERSITY, Guangdong (CN)

( * ) Notice: Subject to any disclaimer, the term of this patent is extended or adjusted under 35 U.S.C. 154(b) by 380 days.

(21) Appl. No.: 16/081,918

(22) PCT Filed: Jan. 9, 2018

(86) PCT No.: PCT/CN2018/071875
§ 371 (c)(1),
(2) Date: Sep. 3, 2018

(87) PCT Pub. No.: WO2019/109458
PCT Pub. Date: Jun. 13, 2019

(65) Prior Publication Data
US 2020/0295274 A1    Sep. 17, 2020

(30) Foreign Application Priority Data

Dec. 6, 2017    (CN) .......................... 201711278799.0

(51) Int. Cl.
*H01L 51/00*    (2006.01)
*H01L 51/50*    (2006.01)
(Continued)

(52) U.S. Cl.
CPC ........ *H01L 51/0074* (2013.01); *C07D 333/76* (2013.01); *C07D 409/12* (2013.01);
(Continued)

(58) Field of Classification Search
CPC .......................... C07D 333/76; H01L 51/0074
See application file for complete search history.

(56) References Cited

FOREIGN PATENT DOCUMENTS

| CN | 105481794 A | * | 4/2016 |
| CN | 105481794 A | | 4/2016 |

OTHER PUBLICATIONS

Machine-generated English-language translation of CN105481794A. (Year: 2016).*

(Continued)

*Primary Examiner* — Vu A Nguyen
(74) *Attorney, Agent, or Firm* — Leong C. Lei

(57) ABSTRACT

An organic monomolecular white light material, a manufacturing method for the same, and an OLED element are provided. The organic monomolecular white light material has a room temperature phosphorescence emission property in a solid state, and can trap triplet exciton to achieve high efficient luminescence. Also, that has a higher thermal decomposition temperature and glass transition temperature, and the synthetic method and purification process thereof are simple. It has the advantages of mild reaction condition and high yield, and the thermal properties, luminescent proper- (Continued)

ties, white-light color purity, etc of a final product can be adjusted by connecting to different aromatic fused ring or aromatic heterocyclic ring groups. In the OLED element, the organic monomolecular white light material is used as an emitting layer, and the emitting layer has a high luminous intensity and a good stability, thus the luminous efficiency and working life of the OLED element achieve practical requirements.

7 Claims, 2 Drawing Sheets

(51) Int. Cl.
*C07D 333/76* (2006.01)
*C07D 409/12* (2006.01)
*C09K 11/06* (2006.01)

(52) U.S. Cl.
CPC .......... *C09K 11/06* (2013.01); *H01L 51/0072* (2013.01); *C09K 2211/1007* (2013.01); *C09K 2211/1011* (2013.01); *C09K 2211/1018* (2013.01); *H01L 51/5012* (2013.01)

(56) References Cited

OTHER PUBLICATIONS

Xu et al., Chem. Sci., 2017, 8, 1909-1914. (Year: 2016).*
SciFinder Search (Year: 2020).*
Xu et al., Chem. Sci., 2017, 8, 1909-1914 (Supplementary Materials). (Year: 2016).*
Alexander et al., Journal of Molecular Catalysis A: Chemical 223 (2004), 75-83. (Year: 2004).*

* cited by examiner

ORGANIC MONOMOLECULAR WHITE LIGHT MATERIAL, MANUFACTURING METHOD FOR THE SAME, AND OLED ELEMENT

BACKGROUND OF THE INVENTION

1. Field of the Invention

The present disclosure relates to a field of display technology, and more specifically to an organic monomolecular white light material, a manufacturing method for the same, and an OLED (organic light-emitting diode) element.

2. Description of the Prior Art

Organic white light materials are the most significant component of an OLED used for a high-resolution flat panel display and a large-area lighting, and thus the design and synthesis of the organic white light materials have been a hot topic in luminescent materials recently, have been paid much attention by the scientific community and industrial community. White light is a compound light formed by mixing the three primary colors of blue, green, and red, or by mixing blue light and yellow light. So far, organic materials having stable white light emission, which is constructed by a mono-molecule and can simultaneously realize luminescence of two colors or three colors, are exceedingly rare, and most of this case occurs in a solution system. Solid-state white light emission produced by mixing various organic molecules has drawbacks of easy to phase separation, poor luminescent stability, complex preparation process, and the like. Therefore, the development of a monomolecular organic white light material stabilized in a solid state is crucial, and has always been concerned.

On the other hand, the theoretical boundary of a quantum efficiency in the element of a fluorescent OLED is only 25% and has over 75% energy loss since the fluorescent OLED based on singlet luminescence can only use injected singlet excitons. However, phosphorescent materials based on triplet luminescence can fully use injected triplet excitons, so that a quantum efficiency in the element of a fluorescent OLED can reach 100%. Pure organic materials are easy to realize phosphorescence emission at low temperatures, but the phosphorescence of most of the materials is disappeared with the enhancement of non-radiation deactivation at room temperature. Currently, most of room temperature phosphorescence materials are coordination complexes formed by nonrenewable noble metal ions according to iridium (Ir), platinum (Pt), and the like, and the high prices thereof lead to considerably increase the preparation costs of an OLED element. Moreover, this kind of the phosphorescence materials is difficult to realize high-quality blue light emission since the triplet energy levels of organometallic coordination complexes are lower. Therefore, most of white-light OLEDs having a room temperature phosphorescence emission property simultaneously use pure organic blue fluorescent materials and yellow phosphorescence coordination complexes as an emitting layer to fully use triplet excitons, thereby realizing mixed luminescence. However, mixing of various luminescent materials certainly leads to worsen the stability of the element, and the working life of the element is significantly affected. Therefore, the development of a novel pure organic monomolecular white light compound having a room temperature phosphorescence emission property in a solid state and the novel pure organic monomolecular white light compound as an emitting layer applied in the OLED element have both significant research meaning and practical value.

SUMMARY OF THE INVENTION

A primary object of the present disclosure is to provide an organic monomolecular white light material, which has a room temperature phosphorescence emission property, which is highly efficient and stable, in a solid state, and the synthetic method and purification process thereof are simple.

Another object of the present disclosure is to provide a method for manufacturing an organic monomolecular white light material. The method has the advantages of mild reaction condition, high yield, easy purification of final product, and adjustment of the thermal stability, the luminous efficiency, the white-light color purity, and the like of a final product by introducing different structural units.

A yet another object of the present disclosure is to provide an OLED element, in which the organic monomolecular white light material is used as an emitting layer, so that the emitting layer has a high luminous intensity and a good stability.

To achieve the above object, the present disclosure provides an organic monomolecular white light emitting material, and the molecule of the organic monomolecular white light emitting material is shown as a formula (1):

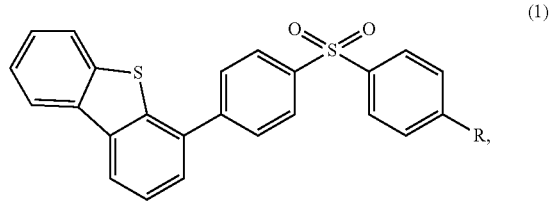

in which R is a hydrogen atom, an aromatic fused ring group, or an aromatic heterocyclic group.

In the molecule of the organic monomolecular white light material, R is selected from the aromatic fused ring group or the aromatic heterocyclic group as follows:

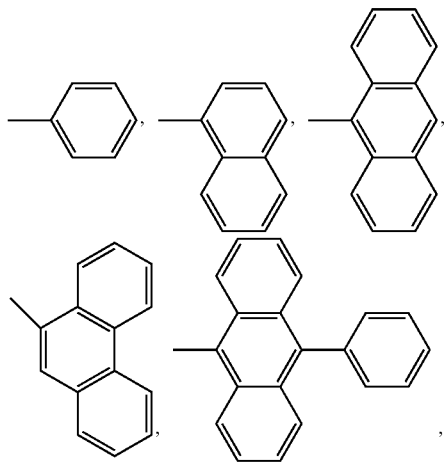

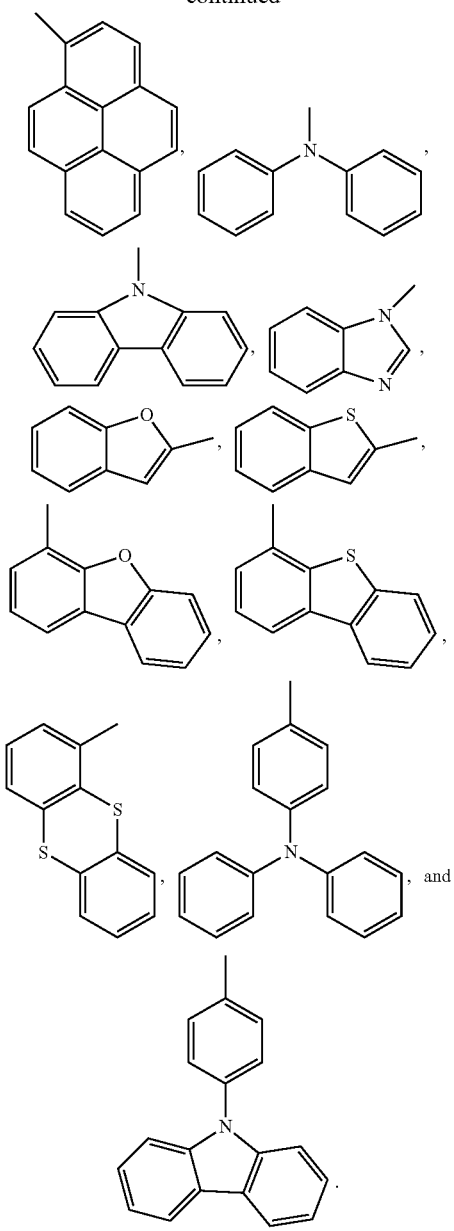

The present disclosure also provides a method for manufacturing an organic monomolecular white light material, which includes:

reacting dibenzothiophene with 1-bromo-4-(benzenesulfonyl)benzene to form a final product which is 4-(4-(benzenesulfonyl)phenyl)dibenzothiophene; or reacting dibenzothiophene with 1-(4-fluorobenzenesulfonyl)-4-bromobenzene or 4,4'-sulfonylbis(bromobenzene) to form an intermediate which is 4-(4-((4-fluorophenyl)sulfonyl)phenyl)dibenzothiophene or 4-(4-((4-bromophenyl)sulfonyl)phenyl)dibenzothiophene, and then reacting the formed intermediate with an aromatic amine, an aromatic fused ring boric acid, or an aromatic heterocyclyl boric acid to form a final product, in which the formed final product is the organic monomolecular white light material, and the molecule of the organic monomolecular white light material is shown as a formula (1):

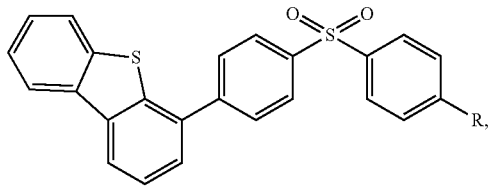

in which R is a hydrogen atom, an aromatic fused ring group, or an aromatic heterocyclic group.

Specifically, the method for manufacturing the organic monomolecular white light material includes the following steps of:

step 1: synthesizing monohalides or dihalides of diphenyl sulfone by a Friedel-Crafts reaction, this is, a first intermediate of 1-bromo-4-(benzenesulfonyl)benzene, a second intermediate of 1-(4-fluorobenzenesulfonyl)-4-bromobenzene, or a fourth intermediate of 4,4'-sulfonylbis(bromobenzene);

step 2: providing dibenzothiophene-4-boric acid, and coupling-reacting dibenzothiophene-4-boric acid with one bromide substituent in the monohalides or dihalides of diphenyl sulfone prepared by the step 1 to form the final product of 4-(4-(benzenesulfonyl)phenyl)dibenzothiophene, a third intermediate of 4-(4-((4-fluorophenyl)sulfonyl)phenyl)dibenzothiophene, or a fifth intermediate of 4-(4-((4-bromophenyl)sulfonyl)phenyl)dibenzothiophene, in which if the third intermediate or the fifth intermediate is obtained in the step 2, step 3 is proceed; and step 3: providing diphenylamine, carbazole, benzimidazole, phenylboronic acid, 1-naphthaleneboronic acid, 9-anthraceneboronic acid, 9-phenanthracenylboronic acid, 10-phenyl-9-anthraceneboronic acid, 1-pyrenylboronic acid, benzofuran-2-boronic acid, benzothiophene-2-boronic acid, dibenzofuran-4-boronic acid, dibenzothiophene-4-boronic acid, thianthrene-1-boronic acid, 4-(Diphenylamino)phenylboronic acid, or 4-(9-carbazolyl)phenylboronic acid, and which is coupling-reacted with the third intermediate or the fifth intermediate prepared by the step 2 to form the final product.

In the molecule of the organic monomolecular white light material, R is the aromatic fused ring group or the aromatic heterocyclic group as follows:

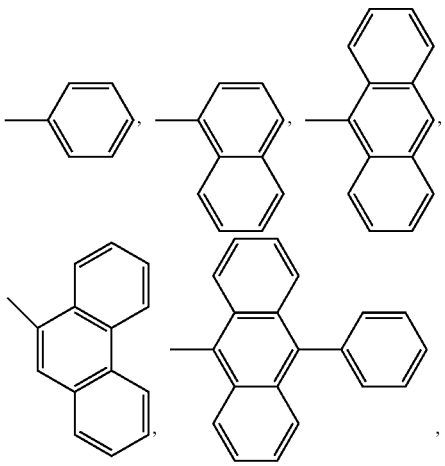

-continued

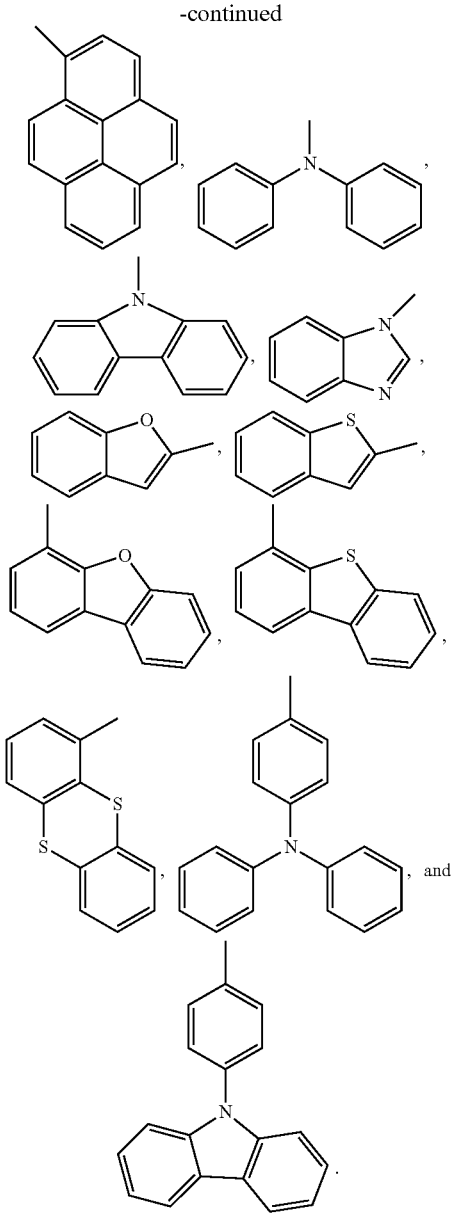

In the step 1, the coupling-reaction of synthesizing the first intermediate, the second intermediate, or the fourth intermediate is implemented by the following method, which includes: providing benzenesulfonyl chloride, 4-bromobenzenesulfonyl chloride and fluorobenzene, or bromobenzene, and then using dichloromethane as a solvent, and connecting fluorobenzene or bromobenzene onto benzenesulfonyl or 4-bromobenzenesulfonyl by the Friedel-Crafts reaction under a catalysis of ferric chloride to form the first intermediate of 1-bromo-4-(benzenesulfonyl)benzene, the second intermediate of 1-(4-fluorobenzenesulfonyl)-4-bromobenzene, or the fourth intermediate of 4,4'-sulfonylbis(bromobenzene).

In the step 2, the coupling-reaction of synthesizing the third intermediate or the fifth intermediate is implemented by the following method, which includes: providing dibenzothiophene-4-boric acid, and then using tetrahydrofuran or toluene as a solvent, and suzuki-coupling-reacting dibenzothiophene-4-boric acid with one bromide substituent in the second intermediate or the fourth intermediate under a catalysis of tetrakis(triphenylphosphine)palladium to form the third intermediate of 4-(4-((4-fluorophenyl)sulfonyl)phenyl)dibenzothiophene or the fifth intermediate of 4-(4-((4-bromophenyl)sulfonyl)phenyl)dibenzothiophene.

In the step 2, the coupling-reaction of synthesizing the final product is implemented by the following method, which includes: providing dibenzothiophene-4-boric acid, and then using tetrahydrofuran or toluene as a solvent, and suzuki-coupling-reacting dibenzothiophene-4-boric acid with the first intermediate under a catalysis of tetrakis (triphenylphosphine)palladium to form the final product of the organic monomolecular white light material.

In the step 3, the coupling-reaction of synthesizing the final product is implemented by the following method, which includes:

providing diphenylamine, carbazole, or benzimidazole, and then using N,N-dimethylformamide as a solvent, and reacting diphenylamine, carbazole, or benzimidazole with the third intermediate under an action of potassium tert-butoxide to form the final product of the organic monomolecular white light material; or providing phenylboronic acid, 1-naphthaleneboronic acid, 9-anthraceneboronic acid, 9-phenanthracenylboronic acid, 10-phenyl-9-anthraceneboronic acid, 1-pyrenylboronic acid, benzofuran-2-boronic acid, benzothiophene-2-boronic acid, dibenzofuran-4-boronic acid, dibenzothiophene-4-boronic acid, thianthrene-1-boronic acid, 4-(Diphenylamino)phenylboronic acid, or 4-(9-carbazolyl)phenylboronic acid, and which is suzuki-coupling-reacted with the fourth intermediate by using tetrahydrofuran or toluene as a solvent under a catalysis of tetrakis(triphenylphosphine)palladium to form the final product of the organic monomolecular white light material.

The present disclosure provides an OLED element, which includes a substrate, a transparent conductive layer, a hole transport layer, an emitting layer, an electron transport layer, and a metal layer. The transparent conductive layer, the hole transport layer, the emitting layer, the electron transport layer, and the metal layer are sequentially disposed on the substrate.

The emitting layer includes an organic monomolecular white light material, and the molecule of the organic monomolecular white light material is shown as a formula (1):

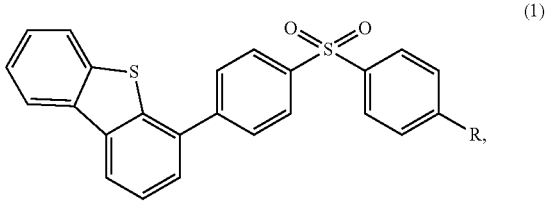

in which R is a hydrogen atom, an aromatic fused ring group, or an aromatic heterocyclic group.

In the molecule of the organic monomolecular white light material, R is selected from the aromatic fused ring group or the aromatic heterocyclic group as follows:

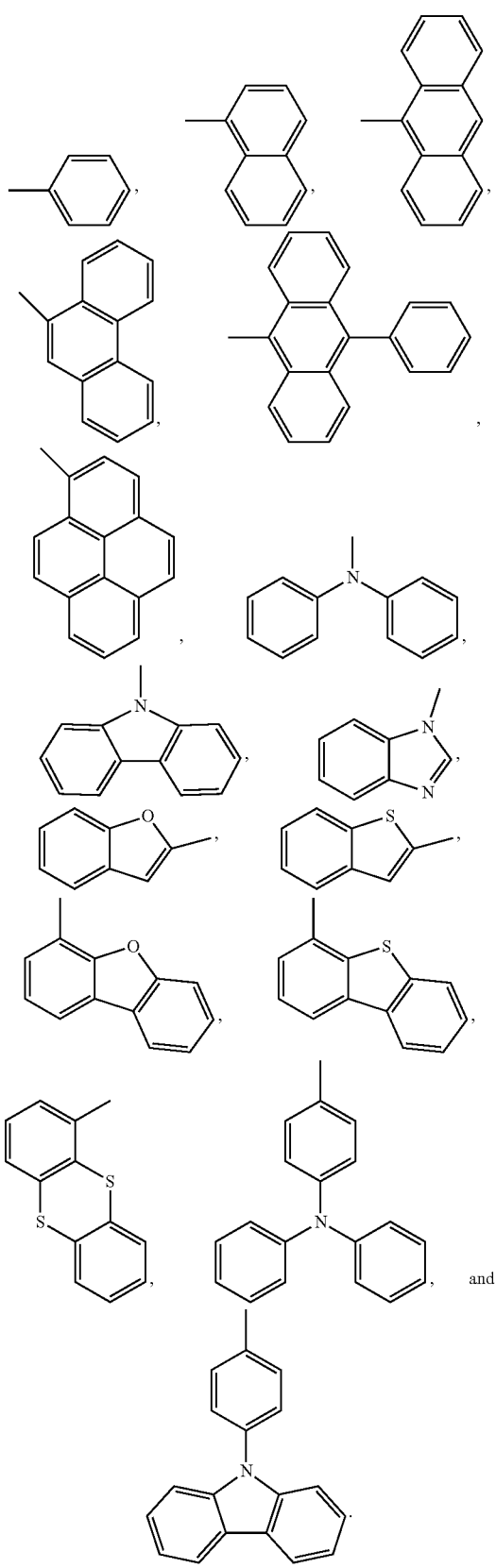

the present disclosure has the room temperature phosphorescence emission property in a solid state, and can trap triplet exciton to achieve high efficient luminescence. Also, the organic monomolecular white light material has a higher thermal decomposition temperature and a higher glass transition temperature, and the synthetic method and purification process thereof are simple. The present disclosure has the advantages of mild reaction condition and high yield, and the thermal properties, the luminescent properties, the white-light color purity, and the like of the final product can be adjusted by connecting to different aromatic fused ring or aromatic heterocyclic ring groups. The method for manufacturing the organic monomolecular white light material of the present disclosure has the advantages of mild reaction condition, high yield, easy purification of the final product, and adjustment of the thermal stability, the luminous efficiency, the white-light color purity, and the like of the final product by introducing different structural units. In the OLED element of the present disclosure, the organic monomolecular white light material is used as an emitting layer, and the emitting layer thereof has a high luminous intensity and a good stability, thus the luminous efficiency and the working life of the OLED element achieve practical requirements.

For better understanding of the features and technical contents of the present disclosure, reference will be made to the following detailed description of the present disclosure and the attached drawings. However, the drawings are provided for the purposes of reference and illustration and are not intended to impose undue limitations to the present disclosure.

BRIEF DESCRIPTION OF THE DRAWINGS

The technical solution, as well as beneficial advantages, of the present disclosure will be apparent from the following detailed description of an embodiment of the present disclosure, with reference to the attached drawings. In the drawings.

DETAILED DESCRIPTION OF THE PREFERRED EMBODIMENTS

To further expound the technical solution adopted in the present disclosure and the advantages thereof, a detailed description is given to a preferred embodiment of the present disclosure and the attached drawings.

The present disclosure provides an organic monomolecular white light material, and the molecule of the organic monomolecular white light material is shown as a formula (1):

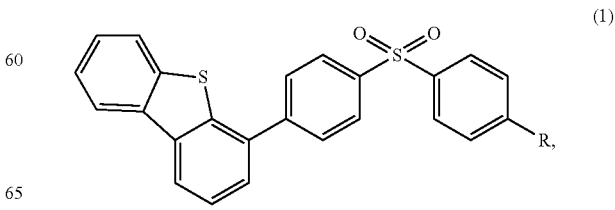

The present disclosure has the following beneficial effects. The organic monomolecular white light material of in which R is a hydrogen atom, an aromatic fused ring group, or an aromatic heterocyclic group.

Specifically, in the molecule of the organic monomolecular white light material, the R is selected from the aromatic fused ring group or the aromatic heterocyclic group as follows:

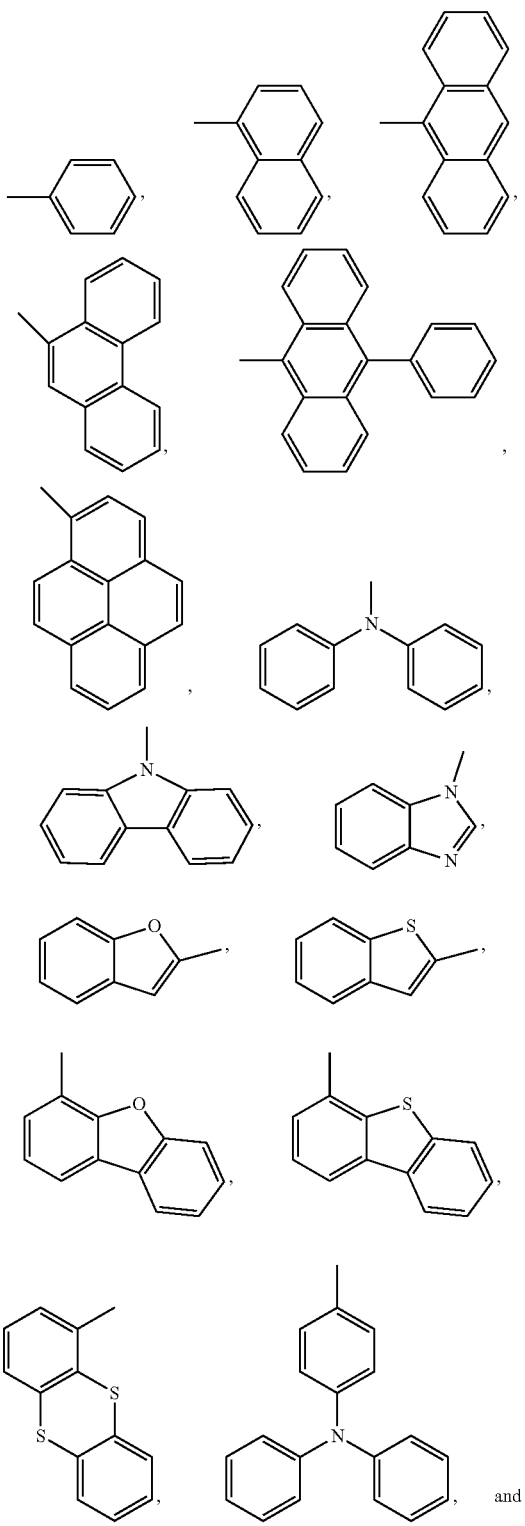

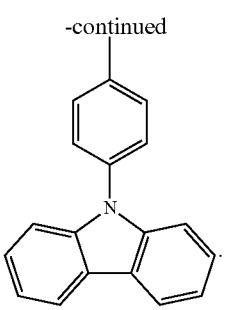

The organic monomolecular white light material of the present disclosure is a pure organic monomolecular white light compound. The organic monomolecular white light material not only includes the group such as a rigid aromatic fused ring, aromatic heterocyclic ring, and the like which are advantageous to improving the thermal stability of materials, but also has a room temperature phosphorescence emission property. Therefore, the organic monomolecular white light material has a good thermal stability, a good luminescent stability, and a high luminous efficiency, and has a characteristic of trapping triplet exciton at room temperature.

Base on the organic monomolecular white light material, the present disclosure also provides a method for manufacturing the organic monomolecular white light material. The method includes:

reacting dibenzothiophene with 1-bromo-4-(benzenesulfonyl)benzene to form a final product which is 4-(4-(benzenesulfonyl)phenyl)dibenzothiophene; or reacting dibenzothiophene with 1-(4-fluorobenzenesulfonyl)-4-bromobenzene or 4,4'-sulfonylbis(bromobenzene) to form an intermediate which is 4-(4-((4-fluorophenyl)sulfonyl)phenyl)dibenzothiophene or 4-(4-((4-bromophenyl)sulfonyl)phenyl)dibenzothiophene, and then reacting the formed intermediate with an aromatic amine, an aromatic fused ring boric acid, or an aromatic heterocyclyl boric acid to form a final product.

The final product prepared by the manufacturing method is the organic monomolecular white light material having the room temperature phosphorescence emission property.

Figure 1:
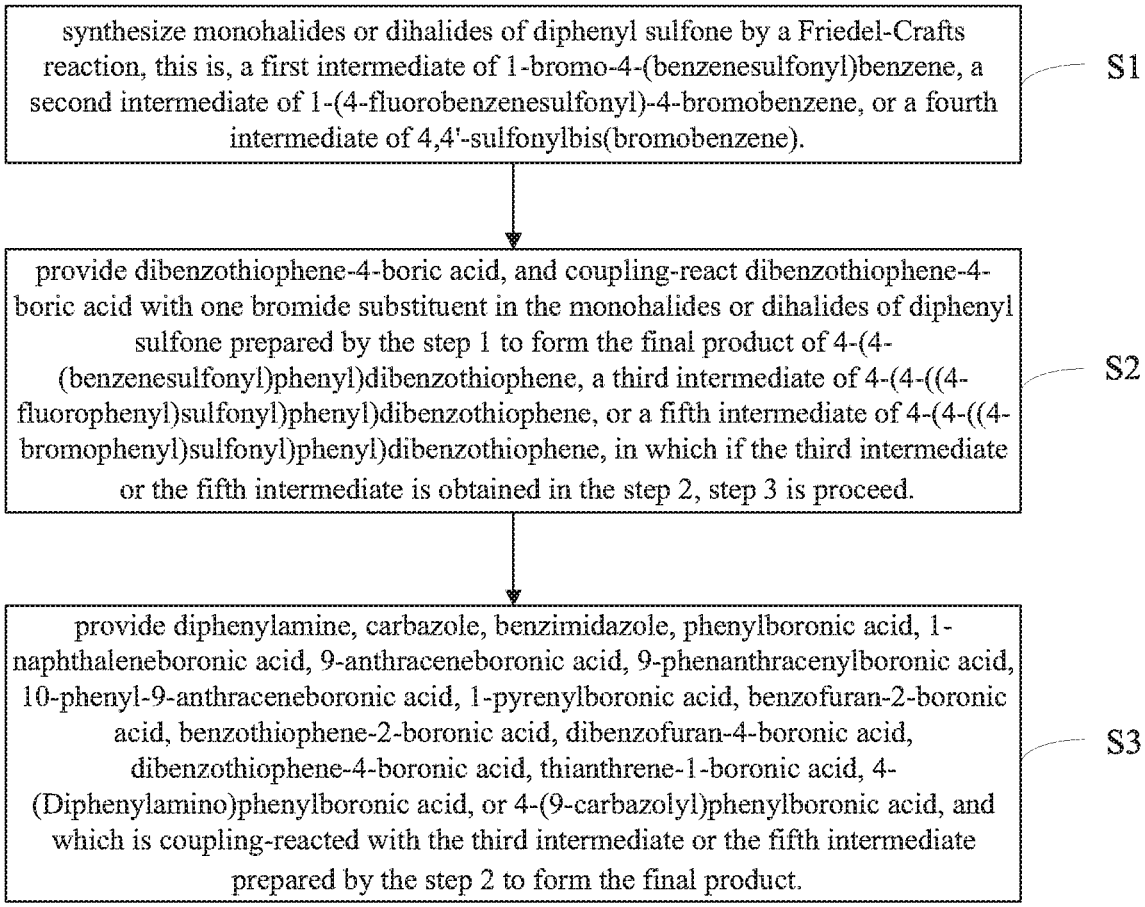
FIG. 1 is a flow chart of a method according to the present disclosure for manufacturing an organic monomolecular white light material.

Please refer to FIG. 1. The method for manufacturing the organic monomolecular white light material of the present disclosure includes the following steps.

In step 1, monohalides or dihalides of diphenyl sulfone are synthesized by a Friedel-Crafts reaction, this is, a first intermediate of 1-bromo-4-(benzenesulfonyl)benzene, a second intermediate of 1-(4-fluorobenzenesulfonyl)-4-bromobenzene, or a fourth intermediate of 4,4'-sulfonylbis(bromobenzene).

Specifically, in the step 1, the coupling-reaction of synthesizing the first intermediate, the second intermediate, or the fourth intermediate is implemented by the following method, which includes: providing benzenesulfonyl chloride, 4-bromobenzenesulfonyl chloride and fluorobenzene, or bromobenzene, and then using dichloromethane (DCM) as a solvent, and connecting fluorobenzene or bromobenzene onto benzenesulfonyl or 4-bromobenzenesulfonyl by the Friedel-Crafts reaction under a catalysis of ferric chloride to form the first intermediate of 1-bromo-4-(benzenesulfonyl)benzene, the second intermediate of 1-(4-fluorobenzenesulfonyl)-4-bromobenzene, or the fourth intermediate of 4,4'-sulfonylbis(bromobenzene).

In step 2, dibenzothiophene-4-boric acid is provided, and dibenzothiophene-4-boric acid is coupling-reacted with one bromide substituent in the monohalides or dihalides of diphenyl sulfone prepared by the step 1 to form the final product of 4-(4-(benzenesulfonyl)phenyl)dibenzothiophene, a third intermediate of 4-(4-((4-fluorophenyl)sulfonyl)phenyl)dibenzothiophene, or a fifth intermediate of 4-(4-((4-bromophenyl)sulfonyl)phenyl)dibenzothiophene. If the third intermediate or the fifth intermediate is obtained in the step 2, step 3 is proceed;

Specifically, in the step 2, the coupling-reaction of synthesizing the third intermediate or the fifth intermediate is implemented by the following method, which includes: providing dibenzothiophene-4-boric acid, and then using tetrahydrofuran or toluene as a solvent, and suzuki-coupling-reacting dibenzothiophene-4-boric acid with one bromide substituent in the second intermediate or the fourth intermediate under a catalysis of tetrakis(triphenylphosphine)palladium to form the third intermediate of 4-(4-((4-fluorophenyl)sulfonyl)phenyl)dibenzothiophene or the fifth intermediate of 4-(4-((4-bromophenyl)sulfonyl)phenyl)dibenzothiophene.

Specifically, in the step 2, the coupling-reaction of synthesizing the final product is implemented by the following method, which includes: providing dibenzothiophene-4-boric acid, and then using tetrahydrofuran or toluene as a solvent, and suzuki-coupling-reacting dibenzothiophene-4-boric acid with the first intermediate under a catalysis of tetrakis(triphenylphosphine)palladium to form the final product of the organic monomolecular white light material.

In step 3, diphenylamine, carbazole, benzimidazole, phenylboronic acid, 1-naphthaleneboronic acid, 9-anthraceneboronic acid, 9-phenanthracenylboronic acid, 10-phenyl-9-anthraceneboronic acid, 1-pyrenylboronic acid, benzofuran-2-boronic acid, benzothiophene-2-boronic acid, dibenzofuran-4-boronic acid, dibenzothiophene-4-boronic acid, thianthrene-1-boronic acid, 4-(Diphenylamino)phenylboronic acid, or 4-(9-carbazolyl)phenylboronic acid is provided, and which is coupling-reacted with the third intermediate or the fifth intermediate prepared by the step 2 to form the final product.

Specifically, in the step 3, the coupling-reaction of synthesizing the final product is implemented by the following method, which includes:
providing diphenylamine, carbazole, or benzimidazole, and then using N,N-dimethylformamide as a solvent, and reacting diphenylamine, carbazole, or benzimidazole with the third intermediate under an action of potassium tert-butoxide to form the final product of the organic monomolecular white light material; or providing phenylboronic acid, 1-naphthaleneboronic acid, 9-anthraceneboronic acid, 9-phenanthracenylboronic acid, 10-phenyl-9-anthraceneboronic acid, 1-pyrenylboronic acid, benzofuran-2-boronic acid, benzothiophene-2-boronic acid, dibenzofuran-4-boronic acid, dibenzothiophene-4-boronic acid, thianthrene-1-boronic acid, 4-(Diphenylamino)phenylboronic acid, or 4-(9-carbazolyl)phenylboronic acid, and which is suzuki-coupling-reacted with the fourth intermediate by using tetrahydrofuran or toluene as a solvent under a catalysis of tetrakis(triphenylphosphine)palladium to form the final product of the organic monomolecular white light material.

Specifically, the molecule of the final product of the organic monomolecular white light material formed by the manufacturing method is shown as a formula (1):

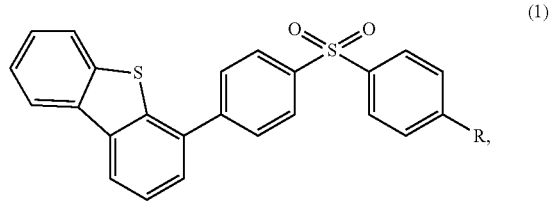

in which R is a hydrogen atom, an aromatic fused ring group, or an aromatic heterocyclic group.

Specifically, in the molecule of the organic monomolecular white light material, the R is selected from the aromatic fused ring group or the aromatic heterocyclic group as follows:

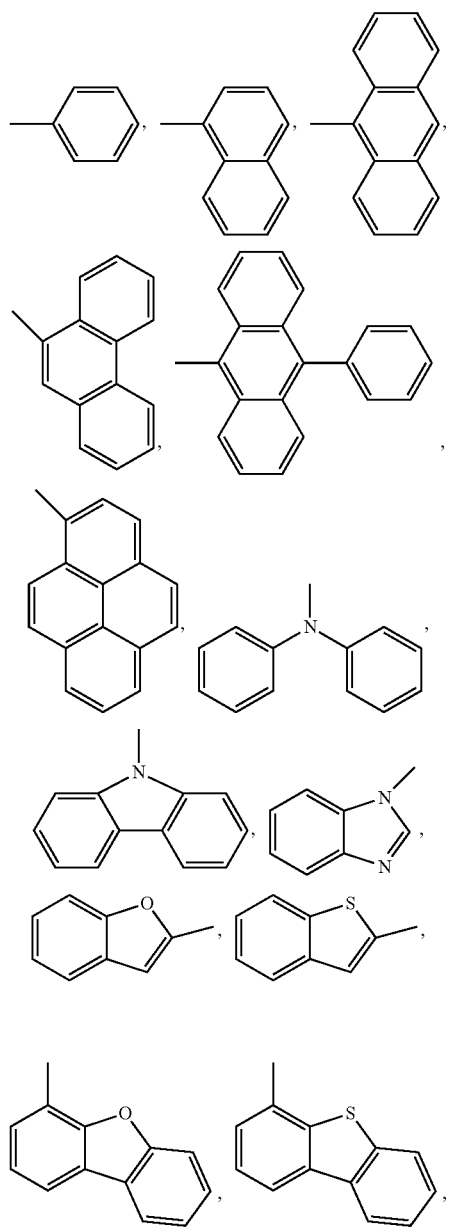

-continued

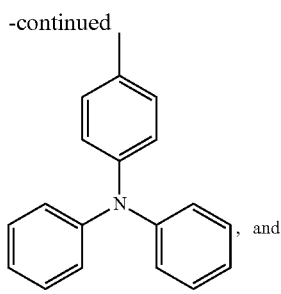

Specifically, in the process of a practical preparation, the thermal properties, the luminescent properties, the white-light color purity, and the like of the product can be adjusted by connecting to different groups on the structure of the selection of R, thereby adapting to the requirements of an actual application.

The method for manufacturing the organic monomolecular white light material will be further illustrated by the following embodiments 1-5, but the present disclosure is not limited thereto.

Embodiment 1: The Synthesis of 4-(4-(benzenesulfonyl)phenyl)dibenzothiophene (1) a first intermediate (i.e., 1-bromo-4-(benzenesulfonyl)benzene) is synthesized, and the synthetic route thereof is shown as the following equation (2):

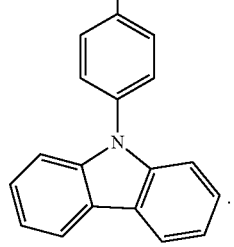 (2)

Benzenesulfonyl chloride (1.00 g, 5.68 mmol) and bromobenzene (1.33 g, 8.52 mmol) are added in 250 mL of a three necked flask, and are dissolved with 20 mL of dichloromethane. Then, after ferric chloride (1.83 g, 11.37 mmol) is added, the reaction mixture is heated to 40° C., and is stirred to react for 6 hours. Then, the reaction mixture is cooled to room temperature, and then 20 mL dichloromethane and 20 mL 1M diluted hydrochloric acid are slowly added, and are stirred for 10 minutes. Then, the mixed solution is poured in a separating funnel, and then the organic layer solution thereof is separated and stored. Also, the water layer solution thereof is extracted three times with dichloromethane, and then is combined in the organic layer solution. Then, the organic layer solution is dried with anhydrous sodium sulfate, and then is filtrated. The solvent in the obtained filtrate is spin-dried by a rotary evaporator, and the crude product thereof is separated and purified by a silica gel column with an eluent, which is the mixed solution of n-hexane and dichloromethane (volume ratio of 4:5). Then, the product thereof is vacuum-dried to obtain 1.46 g of a white powder, and the yield thereof is 87%.

(2) a target product (i.e., 4-(4-(benzenesulfonyl)phenyl)dibenzothiophene) is synthesized, and the synthetic route thereof is shown as the following equation (3):

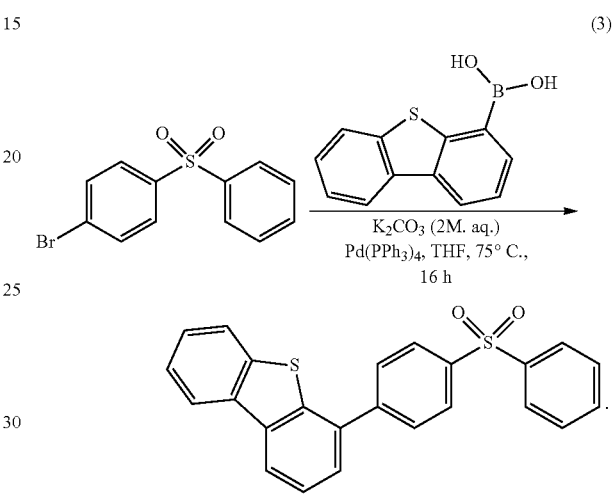 (3)

The first intermediate of 1-bromo-4-(benzenesulfonyl)benzene (1.00 g, 3.38 mmol) and dibenzothiophene-4-boric acid (0.96 g, 4.22 mmol) are added in a three necked flask, and are dissolved with 30 mL of tetrahydrofuran. Then, 4.2 mL of 2M K$_2$CO$_3$ solution is added, and then is stirred for 30 minutes after argon is passed through therein. Then, after 0.05 g of Pd(PPh$_3$)$_4$ is added, the reaction mixture is heated to 75° C., and is reacted for 16 hours. Then, the reaction mixture is cooled to room temperature, and then 20 mL ethyl alcohol is added, and is vacuum-dried by a rotary evaporator. Then, the crude product thereof is separated and purified by a silica gel column with an eluent, which is the mixed solution of n-hexane and dichloromethane (volume ratio of 4:5). The obtained solids are vacuum-dried to obtain 1.09 g of white crystals, and the yield thereof is 81%.

Embodiment 2: The Synthesis of 4-((4-(dibenzothiophene-4-yl)phenyl)sulfonyl)-N,N-diphenylamine (1) a second intermediate (i.e., 1-(4-fluorobenzenesulfonyl)-4-bromobenzene) is synthesized, and the synthetic route thereof is shown as the following equation (4):

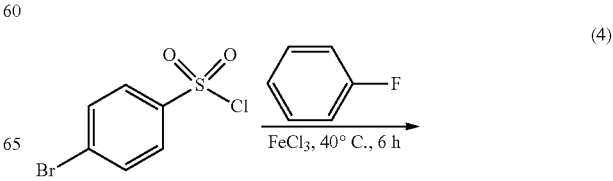 (4)

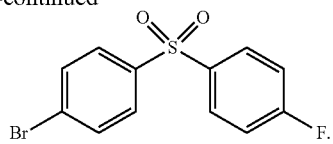

4-bromobenzenesulfonyl chloride (5.00 g, 19.69 mmol) and fluorobenzene (2.84 g, 29.54 mmol) are added in 250 mL of a three necked flask, and are dissolved with 40 mL of dichloromethane. Then, after ferric chloride (6.34 g, 39.39 mmol) is added, the reaction mixture is heated to 40° C., and is stirred to react for 6 hours. Then, the reaction mixture is cooled to room temperature, and then 30 mL dichloromethane and 50 mL 1M diluted hydrochloric acid are slowly added, and are stirred for 10 minutes. Then, the mixed solution is poured in a separating funnel, and then the organic layer solution thereof is separated and stored. Also, the water layer solution thereof is extracted three times with dichloromethane, and then is combined in the organic layer solution. Then, the organic layer solution is dried with anhydrous sodium sulfate, and then is filtrated. The solvent in the obtained filtrate is spin-dried by a rotary evaporator. Then, the remaining solids are vacuum-dried to obtain 5.56 g of a white powder, and the yield thereof is 90%.

(2) a third intermediate (i.e., 4-(4-((4-fluorophenyl)sulfonyl)phenyl)dibenzothiophene) is synthesized, and the synthetic route thereof is shown as the following equation (5):

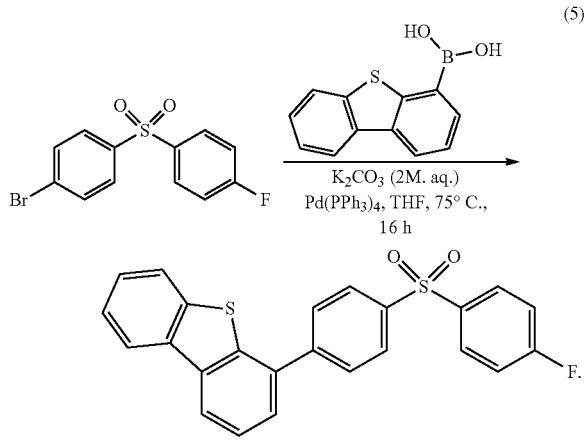

The second intermediate of 1-(4-fluorobenzenesulfonyl)-4-bromobenzene (5.00 g, 15.93 mmol) and dibenzothiophene-4-boric acid (4.54 g, 19.91 mmol) are added in a three necked flask, and are dissolved with 60 mL of tetrahydrofuran (THF). Then, 20 mL of 2M K$_2$CO$_3$ solution is added, and then is stirred for 30 minutes after argon is passed through therein. Then, after 0.10 g of Pd(PPh$_3$)$_4$ is added, the reaction mixture is heated to 75° C., and is reacted for 16 hours. Then, the reaction mixture is cooled to room temperature, and then 40 mL ethyl alcohol is added, and is vacuum-dried by a rotary evaporator. Then, the crude product thereof is separated and purified by a silica gel column with an eluent, which is the mixed solution of n-hexane and dichloromethane (volume ratio of 4:5). The obtained solids are vacuum-dried to obtain 5.06 g of white crystals, and the yield thereof is 76%.

(3) a target product (i.e., 4-((4-(dibenzothiophene-4-yl)phenyl)sulfonyl)-N,N-diphenylamine) is synthesized, and the synthetic route thereof is shown as the following equation (6):

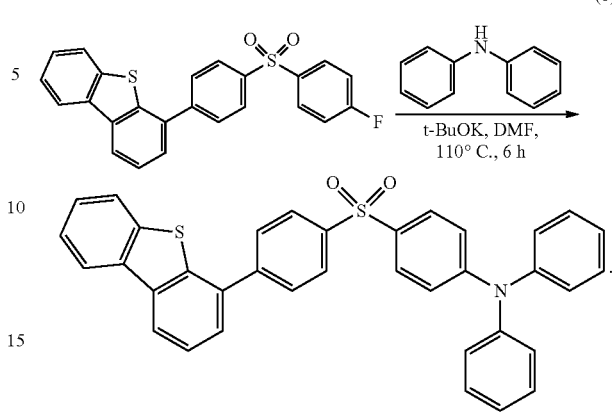

Diphenylamine (0.49 g, 2.87 mmol) is added in a three necked flask, and then 15 mL N,N-dimethylformamide (DMF) and potassium tert-butoxide (0.64 g, 5.74 mmol) are added successively, and are stirred for 20 minutes after argon is passed through therein. Then, after the third intermediate (0.80 g, 1.91 mmol) is added, the reaction mixture is heated to 110° C., and is reacted for 6 hours. Then, the reaction mixture is cooled to room temperature, and is added in 200 mL saturated salt water to separate out solids, and then is filtrated. Then, the crude product thereof is separated and purified by a silica gel column with an eluent, which is the mixed solution of n-hexane and dichloromethane (volume ratio of 1:1). Then, the product thereof is vacuum-dried to obtain 0.93 g of a white powder, and the yield thereof is 85%.

Embodiment 3: The Synthesis of 9-(4-((4-(dibenzothiophene-4-yl)phenyl)sulfonyl)phenyl)-9H-carbazole (1) a target product (i.e., 9-(4-((4-(dibenzothiophene-4-yl)phenyl)sulfonyl)phenyl)-9H-carbazole) is synthesized, and the synthetic route thereof is shown as the following equation (7):

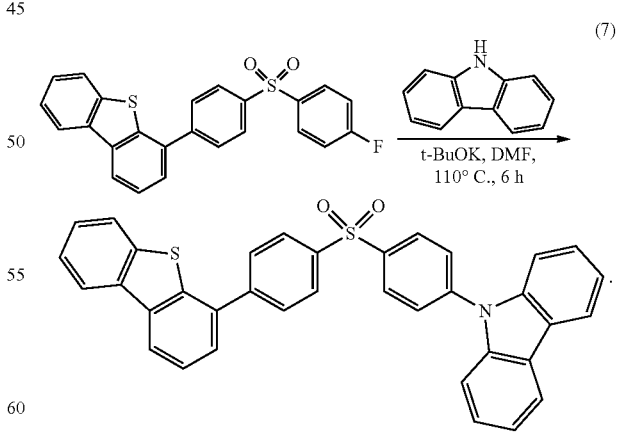

Carbazole (0.48 g, 2.87 mmol) is added in a three necked flask, and then 15 mL N,N-dimethylformamide (DMF) and potassium tert-butoxide (0.64 g, 5.74 mmol) are added successively, and are stirred for 20 minutes after argon is passed through therein. Then, after the third intermediate (0.80 g, 1.91 mmol) is added, the reaction mixture is heated to 110° C., and is reacted for 6 hours. Then, the reaction mixture is cooled to room temperature, and is added in 200 mL saturated salt water to separate out solids, and then is filtered. Then, the crude product thereof is separated and purified by a silica gel column with an eluent, which is the mixed solution of n-hexane and dichloromethane (volume ratio of 1:1). Then, the product thereof is vacuum-dried to obtain 0.89 g of a white powder, and the yield thereof is 82%.

Embodiment 4: The Synthesis of 4,4'-(sulfonylbis (4,1-phenyl))dibenzothiophene (1) a fourth intermediate (i.e., 4,4'-sulfonylbis(bromobenzene)) is synthesized, and the synthetic route thereof is shown as the following equation (8):

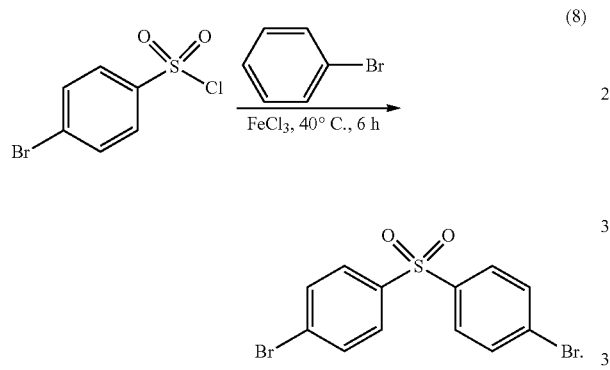

(8)

4-bromobenzenesulfonyl chloride (5.00 g, 19.69 mmol) and bromobenzene (4.61 g, 29.54 mmol) are added in 250 mL of a three necked flask, and are dissolved with 40 mL of dichloromethane. Then, after ferric chloride (6.34 g, 39.39 mmol) is added, the reaction mixture is heated to 40° C., and is stirred to react for 6 hours. Then, the reaction mixture is cooled to room temperature, and then 30 mL dichloromethane and 50 mL 1M diluted hydrochloric acid are slowly added, and are stirred for 10 minutes. Then, the mixed solution is poured in a separating funnel, and then the organic layer solution thereof is separated and stored. Also, the water layer solution thereof is extracted three times with dichloromethane, and then is combined in the organic layer solution. Then, the organic layer solution is dried with anhydrous sodium sulfate, and then is filtered. The solvent in the obtained filtrate is spin-dried by a rotary evaporator, and the crude product thereof is separated and purified by a silica gel column with an eluent, which is the mixed solution of n-hexane and dichloromethane (volume ratio of 4:5). Then, the product thereof is vacuum-dried to obtain 6.48 g of a white powder, and the yield thereof is 88%.

(2) a fifth intermediate (i.e., 4-(4-((4-bromophenyl)sulfonyl)phenyl)dibenzothiophene) is synthesized, and the synthetic route thereof is shown as the following equation (9):

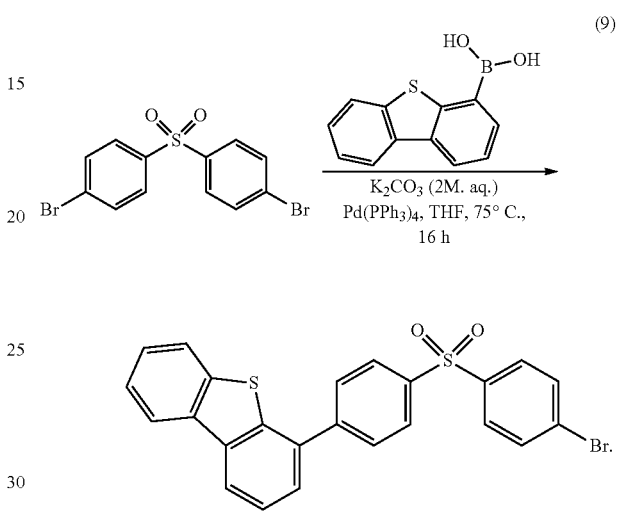

(9)

The fourth intermediate of 4,4'-sulfonylbis(bromobenzene) (4.92 g, 13.16 mmol) and dibenzothiophene-4-boric acid (2.00 g, 8.77 mmol) are added in a three necked flask, and are dissolved with 50 mL of tetrahydrofuran (THF). Then, 8.7 mL of 2M K$_2$CO$_3$ solution is added, and then is stirred for 30 minutes after argon is passed through therein. Then, after 0.10 g of Pd(PPh$_3$)$_4$ is added, the reaction mixture is heated to 75° C., and is reacted for 16 hours. Then, the reaction mixture is cooled to room temperature, and then 30 mL ethyl alcohol is added, and is vacuum-dried by a rotary evaporator. Then, the crude product thereof is separated and purified by a silica gel column with an eluent, which is the mixed solution of n-hexane and dichloromethane (volume ratio of 4:5). The obtained solids are vacuum-dried to obtain 2.01 g of a white powder, and the yield thereof is 48%.

(3) a target product (i.e., 4,4'-(sulfonylbis(4,1-phenyl)) dibenzothiophene) is synthesized, and the synthetic route thereof is shown as the following equation (10):

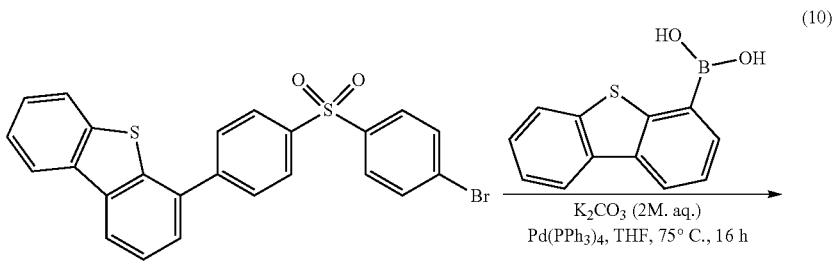

(10)

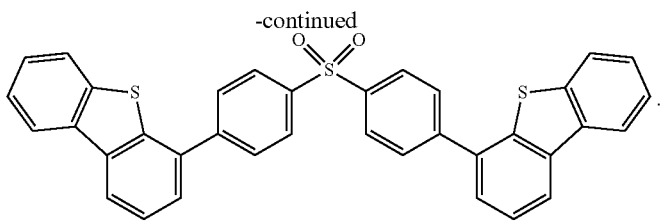

The fifth intermediate of 4-(4-((4-bromophenyl)sulfonyl) phenyl)dibenzothiophene (0.50 g, 1.05 mmol) and dibenzothiophene-4-boric acid (0.30 g, 1.31 mmol) are added in a three necked flask, and are dissolved with 30 mL of tetrahydrofuran (THF). Then, 1.3 mL of 2M $K_2CO_3$ solution is added, and then is stirred for 30 minutes after argon is passed through therein. Then, after 0.05 g of Pd(PPh$_3$)$_4$ is added, the reaction mixture is heated to 75° C., and is reacted for 16 hours. Then, the reaction mixture is cooled to room temperature, and then 15 mL ethyl alcohol is added, and is vacuum-dried by a rotary evaporator. Then, the crude product thereof is separated and purified by a silica gel column with an eluent, which is the mixed solution of n-hexane and dichloromethane (volume ratio of 1:1). The obtained solids are vacuum-dried to obtain 0.45 g of a white powder, and the yield thereof is 74%.

Embodiment 5: The Synthesis of 4-(4-((4-(phenanthren-9-yl)phenyl)sulfonyl)phenyl)dibenzothiophene (1) a target product (i.e., 4-(4-((4-(phenanthren-9-yl)phenyl)sulfonyl)phenyl)dibenzothiophene) is synthesized, and the synthetic route thereof is shown as the following equation (11):

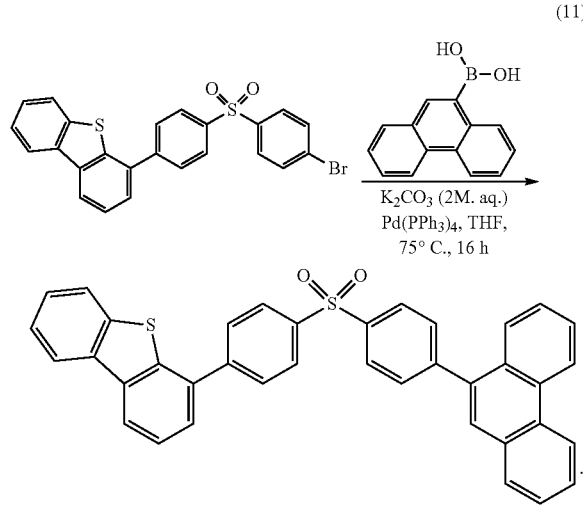

(11)

The fifth intermediate of 4-(4-((4-bromophenyl)sulfonyl) phenyl)dibenzothiophene (0.50 g, 1.05 mmol) and 9-phenanthracenylboronic acid (0.29 g, 1.31 mmol) are added in a three necked flask, and are dissolved with 30 mL of tetrahydrofuran (THF). Then, 1.3 mL of 2M $K_2CO_3$ solution is added, and then is stirred for 30 minutes after argon is passed through therein. Then, after 0.05 g of Pd(PPh$_3$)$_4$ is added, the reaction mixture is heated to 75° C., and is reacted for 16 hours. Then, the reaction mixture is cooled to room temperature, and then 15 mL ethyl alcohol is added, and is vacuum-dried by a rotary evaporator. Then, the crude product thereof is separated and purified by a silica gel column with an eluent, which is the mixed solution of n-hexane and dichloromethane (volume ratio of 1:1). The obtained solids are vacuum-dried to obtain 0.39 g of a white powder, and the yield thereof is 65%.

For better illustrating of the performance of the organic monomolecular white light material of the present disclosure, the performance of target products synthesized by the embodiments 1-5 is tested. That focuses on the thermal properties, light-emitting wavelengths, and color coordinates of the target products, and the results thereof are shown as Table 1.

TABLE 1

| compound | $T_{d,5\%}$ (° C.) | $T_g$ (° C.) | $\Phi_{F,s}$ (%) | $\lambda_{em}$ (nm) | $CIE_{x,y}$ | room temperature phosphorescence emission property contained |
|---|---|---|---|---|---|---|
| embodiment 1 | 332 | 63 | 10 | 384; 520 | (0.24, 0.25) | yes |
| embodiment 2 | 393 | 115 | 68 | 412; 550 | (0.25, 0.27) | yes |
| embodiment 3 | 420 | 122 | 73 | 410; 550 | (0.26, 0.26) | yes |
| embodiment 4 | 446 | 119 | 42 | 392; 547 | (0.27, 0.27) | yes |
| embodiment 5 | 458 | 124 | 28 | 405; 556 | (0.29, 0.27) | yes |

$T_{d,5}\%$ is a temperature which is under nitrogen atmosphere, and when the weightlessness is 5%. $T_{d,5}\%$ is measured by a TGA-50H thermal gravimetric analyzer of Shimadzu Corporation (Japan), and the nitrogen flow rate thereof is 20 mL/min. $T_g$ is a glass transition temperature. $T_g$ is measured by a differential scanning calorimetry (DSC) with a DSC 204F1 differential scanning calorimeter of NETZSCH Corporation (Germany), and the heating rate thereof is 10° C./min. $CIE_{x,y}$ is a color coordinate, and is measured by a Photo Research Spectra Scan PR655 colorimeter. $\Phi_{F,s}$ is a fluorescence quantum efficiency of a solid powder, and is measured by the fluorescence quantum yield testing system of a Horiba JY FluoroLog-3 fluorescence spectrometer.

By the data of the table above, the organic monomolecular white light materials of the present disclosure have a good thermal stability, and the fluorescence quantum yield, the white-light color purity, and the like of the final product can be adjusted by introducing different substituents.

Therefore, the organic monomolecular white light material of the present disclosure is very suitable for an emitting layer material in an OLED.

Figure 2:
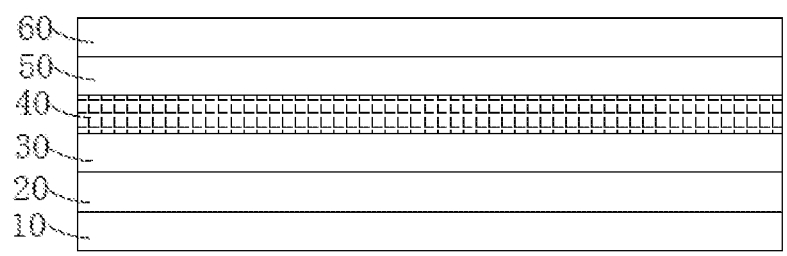
FIG. 2 is a schematic view of a structure of an OLED element according to the present disclosure.

Therefore, the present disclosure further provides an OLED element, in which the organic monomolecular white light material is used as an emitting layer. Please refer to FIG. 2, the OLED element includes a substrate 10, a transparent conductive layer 20, a hole transport layer 30, an emitting layer 40, an electron transport layer 50, and a metal layer 60. The transparent conductive layer 20, the hole transport layer 30, the emitting layer 40, the electron transport layer 50, and the metal layer 60 are sequentially disposed on the substrate 10. The emitting layer 50 is the organic monomolecular white light material, and the molecule of the organic monomolecular white light material is shown as a formula (1):

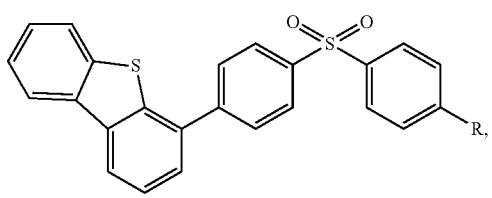

(1)

in which R is a hydrogen atom, an aromatic fused ring group, or an aromatic heterocyclic group.

Specifically, in the molecule of the organic monomolecular white light material, the R is selected from the aromatic fused ring group or the aromatic heterocyclic group as follows:

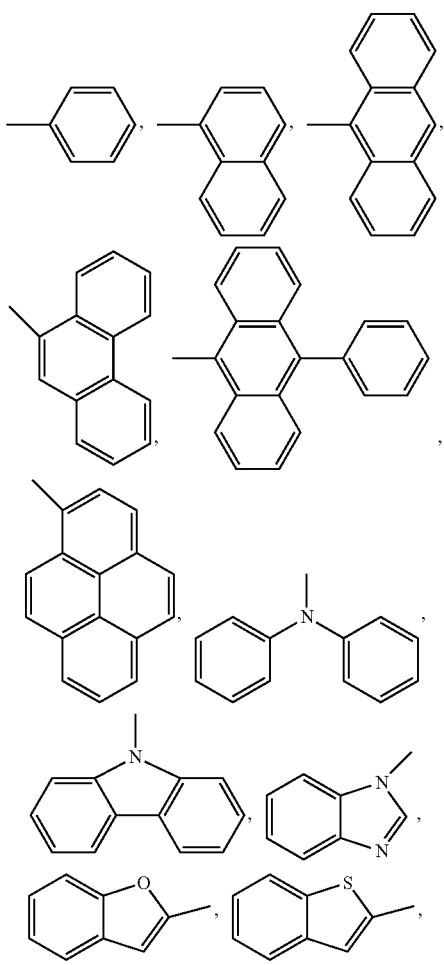

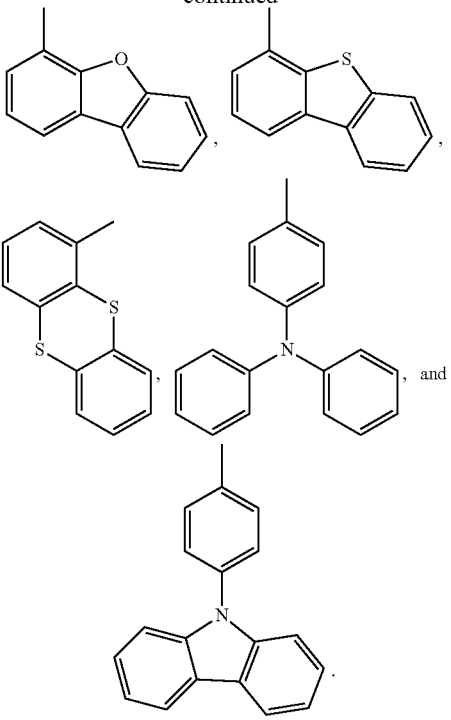

The luminous efficiency and the working life of the OLED element achieve practical requirements since the organic monomolecular white light material used in the emitting layer 50 has a high fluorescence quantum yield and a good thermal stability in the OLED element of the present disclosure.

As mentioned above, the organic monomolecular white light material of the present disclosure has the room temperature phosphorescence emission property in a solid state, and can trap triplet exciton to achieve high efficient luminescence. Also, the organic monomolecular white light material has a higher thermal decomposition temperature and a higher glass transition temperature, and the synthetic method and purification process thereof are simple. The present disclosure has the advantages of mild reaction condition and high yield, and the thermal properties, the luminescent properties, the white-light color purity, and the like of the final product can be adjusted by connecting to different aromatic fused ring or aromatic heterocyclic ring groups. The method for manufacturing the organic monomolecular white light material of the present disclosure has the advantages of mild reaction condition, high yield, easy purification of the final product, and adjustment of the thermal stability, the luminous efficiency, the white-light color purity, and the like of the final product by introducing different structural units. In the OLED element of the present disclosure, the organic monomolecular white light material is used as an emitting layer, and the emitting layer thereof has a high luminous intensity and a good stability, thus the luminous efficiency and the working life of the OLED element achieve practical requirements.

Based on the description given above, those having ordinary skills of the art may easily contemplate various changes and modifications of the technical solution and technical ideas of the present disclosure and all these changes and modifications are considered within the protection scope of right for the present disclosure.

What is claimed is:

1. An organic monomolecular white light material, wherein a molecule of the organic monomolecular white light material is shown as a formula (1):

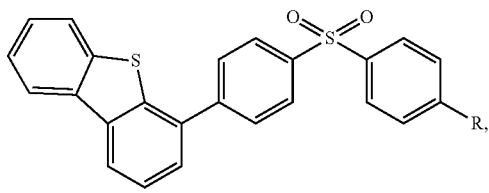

(1)

wherein R is selected from a group consisting of the following:

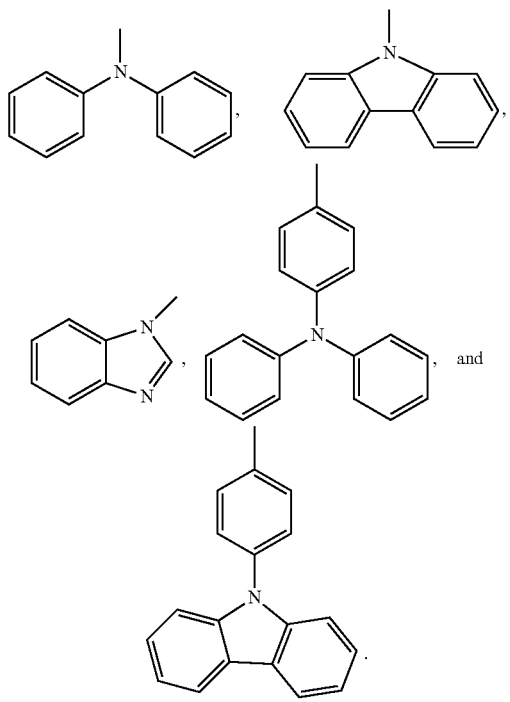

2. A method for manufacturing an organic monomolecular white light material, comprising:
reacting dibenzothiophene with 1-bromo-4-(benzenesulfonyl)benzene to form a final product which is 4-(4-(benzenesulfonyl)phenyl)dibenzothiophene; or reacting dibenzothiophene with 1-(4-fluorobenzenesulfonyl)-4-bromobenzene or 4,4'-sulfonylbis(bromobenzene) to form an intermediate which is 4-(4-((4-fluorophenyl)sulfonyl)phenyl)dibenzothiophene or 4-(4-((4-bromophenyl)sulfonyl)phenyl)dibenzothiophene, and then reacting the formed intermediate with an aromatic amine, an aromatic fused ring boric acid, or an aromatic heterocyclyl boric acid to form a final product,
wherein the formed final product is the organic monomolecular white light material, and a molecule of the organic monomolecular white light material is shown as a formula (1):

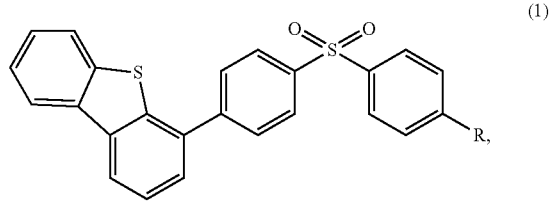

(1)

wherein R is selected from a group consisting of the following:

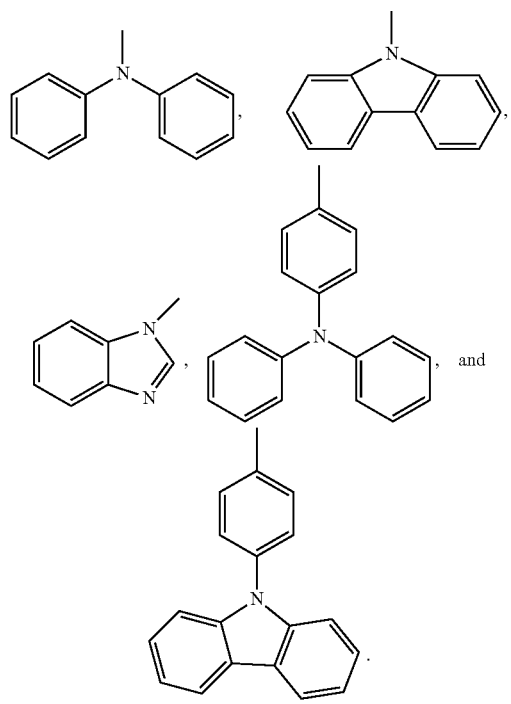

3. The method for manufacturing the organic monomolecular white light material of claim 2, wherein the method comprises the following steps of:
step 1: employing a Friedel-Crafts reaction for synthesizing monohalides or dihalides of diphenyl sulfone, which is, a first intermediate of 1-bromo-4-(benzenesulfonyl)benzene, a second intermediate of 1-(4-fluorobenzenesulfonyl)-4-bromobenzene, or a fourth intermediate of 4,4'-sulfonylbis(bromobenzene);
step 2: providing dibenzothiophene-4-boric acid, and coupling-reacting dibenzothiophene-4-boric acid with one bromide substituent in the monohalides or dihalides of diphenyl sulfone prepared by the step 1 to form the final product of 4-(4-(benzenesulfonyl)phenyl)dibenzothiophene, a third intermediate of 4-(4-((4-fluorophenyl)sulfonyl)phenyl)dibenzothiophene, or a fifth intermediate of 4-(4-((4-bromophenyl)sulfonyl)phenyl) dibenzothiophene, wherein if the third intermediate or the fifth intermediate is obtained in the step 2, step 3 is proceeded; and
step 3: providing diphenylamine, carbazole, benzimidazole, phenylboronic acid, 1-naphthaleneboronic acid, 9-anthraceneboronic acid, 9-phenanthracenylboronic acid, 10-phenyl-9-anthraceneboronic acid, 1-pyrenylboronic acid, benzofuran-2-boronic acid, benzothiophene-2-boronic acid, dibenzofuran-4-boronic acid, dibenzothiophene-4-boronic acid, thianthrene-l-boronic acid, 4-(Diphenylamino)phenylboronic acid, or 4-(9-carbazolyl)phenylboronic acid, and which is coupling-reacted with the third intermediate or the fifth intermediate prepared by the step 2 to form the final product.

4. The method for manufacturing the organic monomolecular white light material of claim 3, wherein in the step 1, a coupling-reaction of synthesizing the first intermediate, the second intermediate, or the fourth intermediate is implemented by the following method, which comprises:
providing benzenesulfonyl chloride, or a combination of 4-bromobenzenesulfonyl chloride and fluorobenzene, or bromobenzene, and then using dichloromethane as a solvent, and connecting fluorobenzene or bromobenzene onto benzenesulfonyl or 4-bromobenzenesulfonyl by the Friedel-Crafts reaction under a catalysis of ferric chloride to form the first intermediate of 1-bromo-4-(benzenesulfonyl)benzene, the second intermediate of 1-(4-fluorobenzenesulfonyl)-4-bromobenzene, or the fourth intermediate of 4,4'-sulfonylbis(bromobenzene).

5. The method for manufacturing the organic monomolecular white light material of claim 3, wherein in the step 2, a coupling-reaction of synthesizing the third intermediate or the fifth intermediate is implemented by the following method, which comprises: providing dibenzothiophene-4-boric acid, and then using tetrahydrofuran or toluene as a solvent, and suzuki-coupling-reacting dibenzothiophene-4-boric acid with one bromide substituent in the second intermediate or the fourth intermediate under a catalysis of tetrakis(triphenylphosphine)palladium to form the third intermediate of 4-(4-((4-fluorophenyl)sulfonyl)phenyl)dibenzothiophene or the fifth intermediate of 4-(4-((4-bromophenyl)sulfonyl)phenyl)dibenzothiophene.

6. The method for manufacturing the organic monomolecular white light material of claim 3, wherein in the step 2, a coupling-reaction of synthesizing the final product is implemented by the following method, which comprises: providing dibenzothiophene-4-boric acid, and then using tetrahydrofuran or toluene as a solvent, and suzuki-coupling-reacting dibenzothiophene-4-boric acid with the first intermediate under a catalysis of tetrakis(triphenylphosphine)palladium to form the final product of the organic monomolecular white light material;
in the step 3, a coupling-reaction of synthesizing the final product is implemented by the following method, which comprises:
providing diphenylamine, carbazole, or benzimidazole, and then using N,N-dimethylformamide as a solvent, and reacting diphenylamine, carbazole, or benzimidazole with the third intermediate under an action of potassium tert-butoxide to form the final product of the organic monomolecular white light material; or providing phenylboronic acid, 1-naphthaleneboronic acid, 9-anthraceneboronic acid, 9-phenanthracenylboronic acid, 10-phenyl-9-anthraceneboronic acid, 1-pyrenylboronic acid, benzofuran-2-boronic acid, benzothiophene-2-boronic acid, dibenzofuran-4-boronic acid, dibenzothiophene-4-boronic acid, thianthrene-l-boronic acid, 4-(Diphenylamino)phenylboronic acid, or 4-(9-carbazolyl)phenylboronic acid, and which is suzuki-coupling-reacted with the fourth intermediate by using tetrahydrofuran or toluene as a solvent under a catalysis of tetrakis(triphenylphosphine)palladium to form the final product of the organic monomolecular white light material.

7. An OLED (organic light-emitting diode) element, comprising a substrate, a transparent conductive layer, a hole transport layer, an emitting layer, an electron transport layer, and a metal layer, wherein the transparent conductive layer, the hole transport layer, the emitting layer, the electron transport layer, and the metal layer are sequentially disposed on the substrate; and
the emitting layer comprises an organic monomolecular white light material, and a molecule of the organic monomolecular white light material is shown as a formula (1):

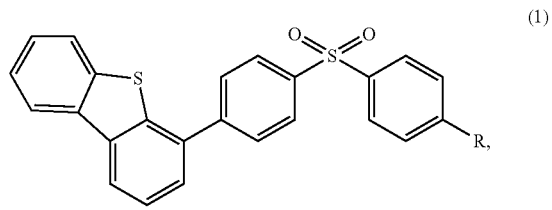

(1)

wherein R is selected from a group consisting of the following:

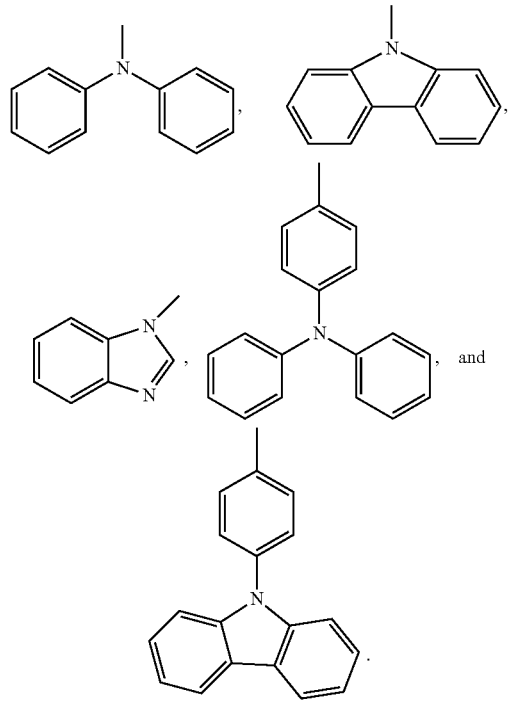

* * * * *